United States Patent [19]
Kamerling

[11] Patent Number: 5,569,280
[45] Date of Patent: Oct. 29, 1996

[54] OPHTHALMIC TEMPLATE

[76] Inventor: William H. Kamerling, 423 Clements Bridge Rd., Barrington, N.J. 08007

[21] Appl. No.: 276,853
[22] Filed: Jun. 29, 1994
[51] Int. Cl.⁶ .................................................. A61B 17/32
[52] U.S. Cl. ............................................ 606/166; 606/107
[58] Field of Search .................................. 606/166, 169, 606/1, 107, 167, 170, 171

[56] References Cited

U.S. PATENT DOCUMENTS

| 4,619,259 | 10/1986 | Graybill | 128/305 |
| 5,135,530 | 8/1992 | Lehmer | 606/107 |
| 5,171,254 | 12/1992 | Sher | 606/166 |
| 5,269,787 | 12/1993 | Cozean, Jr. et al. | 606/107 |

FOREIGN PATENT DOCUMENTS 2588751  4/1987  France ........................ 606/166

Primary Examiner—Michael Powell Buiz
Assistant Examiner—Mark S. Leonardo
Attorney, Agent, or Firm—Stuart E. Beck

[57] ABSTRACT

An ophthalmic template that is used for cutting an opening in the anterior capsule of the eye. It comprises a first member that has the same shape as the opening that is to be cut. A vacuum selectively retains the first member on the anterior capsule. A conduit introduces irrigating fluid into the anterior chamber to keep it formed. A method of making an opening in the anterior capsule of the eye including the steps of placing a template on the anterior capsule in the place where the opening is to be made, retaining the template in place, and removing the portion of said anterior capsule adjacent to the template.

13 Claims, 1 Drawing Sheet

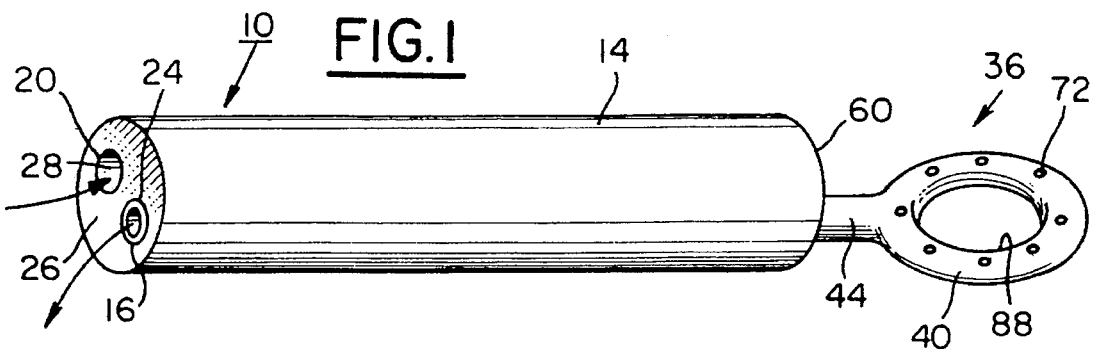
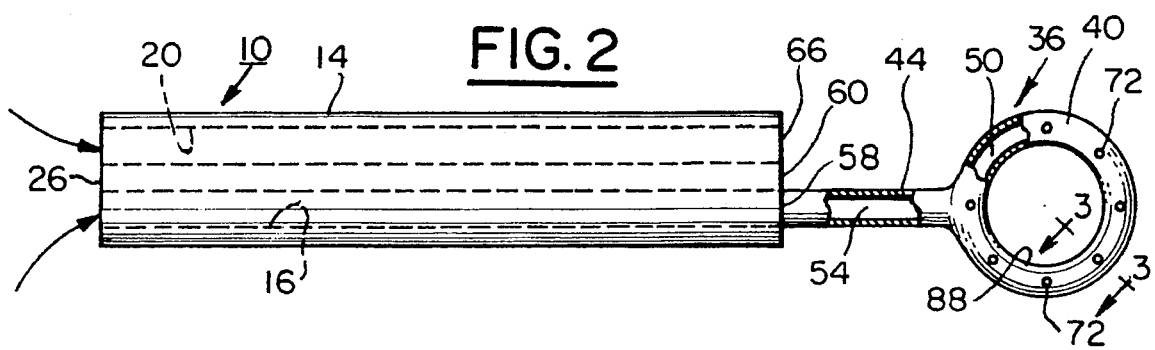
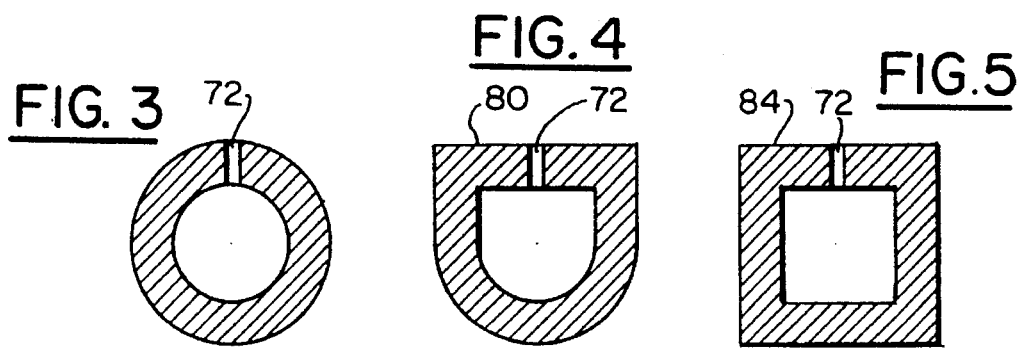
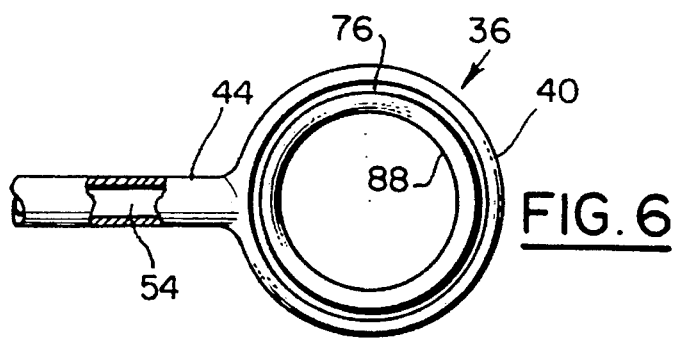

OPHTHALMIC TEMPLATE

BACKGROUND OF THE INVENTION

This invention relates to an instrument for performing eye surgery, more particularly to a template which enables the ophthalmic surgeon to carefully remove portions of the anterior capsule during surgical removal of a cataract through a small incision.

From time to time the lens of the eye becomes opacified to the extent that vision is impaired. Opacified lenses are termed cataracts.

There is no presently known technology or treatment which will reverse the opacification of the lens. Accordingly, the preferred method of treatment for cataracts has been to surgically remove the lens and then to compensate for that removal by the substitution of an artificial lens.

The lens comprises a capsule which includes anterior and posterior portions. The capsule contains a nucleus surrounded by a cortex. The nucleus is comprised of relatively hard material while the cortex is a jelly-like material.

There are several surgical methods for removing cataracts. They are described in my U.S. Pat. No. 5,217,459.

As explained in that patent, during cataract surgery, it is necessary to form a circular opening in the anterior capsule. This procedure is known as a "capsulorhexis".

Many surgeons have difficulty using this procedure since the capsulorhexis includes the step of tearing a circular opening in the anterior capsule that has a diameter of no greater than about five or six millimeters in diameter. Further, to reach the anterior capsule, an incision of about three millimeters in length must be cut in the eye. This is to enable a small tool to fit through the incision and then to tear the opening in the anterior capsule.

There is concern on the part of ophthalmic surgeons that the opening in the anterior capsule will not be correctly formed. Thus, it may be in the wrong place or be of irregular shape, over or under-sized, or have jagged edges.

If the opening in the anterior capsule is too small, it is more difficult to remove the cataract. Further, there is a possibility that the opening will further constrict at a later date making vision more difficult.

On the other hand, if the opening in the anterior capsule is too large, the tear may extend from the anterior capsule around to the posterior capsule. This may lead to complications during surgery such as loss of the nucleus into the posterior segment of the eye, or de-centering of the interocular lens implant at a later date.

It would be advantageous to have an instrument which would avoid these problems while at the same time being capable of fitting through the small incision necessary to enter the eye while at the same time providing a template which will permit the accurate making of an opening in the anterior capsule having a diameter of about five or six millimeters. Further, additional advantages would flow if the instrument were made of inexpensive materials so that it could be discarded after use.

With the foregoing in mind the invention relates generally to an ophthalmic template for use in making an opening in the anterior capsule of the eye that comprises a member that includes an edge that has a shape that corresponds to the shape of the opening that is to be made in the anterior capsule. It also includes means for selectively retaining the member on the anterior capsule.

In another aspect, the invention relates to a method for making an opening in the anterior capsule of the eye comprising the steps of placing a template on the anterior capsule in the place where the opening is to be made, retaining the template in place, and removing the portion of the anterior capsule adjacent the template.

BRIEF DESCRIPTION OF THE DRAWING

The invention will be better understood and further advantages and uses of it will be readily apparent when considered in view of the following description of exemplary embodiments, taken with the accompanying drawing in which:

FIG. 1 is a pictorial view of one presently preferred embodiment of the invention.

FIG. 2 is a plan view of the device illustrated in FIG. 1.

FIG. 3 is a section view taken along line 3—3 of FIG. 2.

FIG. 4 is a view similar to FIG. 3, however, but of a different embodiment of the invention.

FIG. 5 is a view similar to FIG. 3 but of a still further embodiment of the invention.

FIG. 6 is a view similar to FIG. 2 but of an other embodiment of the invention.

DESCRIPTION OF THE PREFERRED EMBODIMENT

Referring now to FIG. 1 an ophthalmic template 10 constructed in accordance with a presently preferred embodiment of the invention is seen to comprise a base 14. The base may be an elongated cylindrical member having a diameter of about eight millimeters.

The base 14 may be comprised of an inexpensive lightweight metal or plastic. It includes first and second conduits 16 and 20. Preferably, the conduits are formed integrally with the base 14. Conduit 16 defines an opening 24 in end face 26 of the base while conduit 20 defines an opening 28 in the end face.

The template 36 comprises a hollow annulus 40 which has an outer diameter of about six millimeters and an inner diameter of about five millimeters. A radially outwardly directed hollow tube 44 may be formed integrally with the hollow annulus 40. The annulus 40 and tube 44 may each have a diameter of about one half to one millimeter in cross section. They may be made from rubber, neoprene, or other suitable flexible, resilient material. The interior passageway 50 in the annulus 40 is connected to the interior passageway 54 in the hollow tube 44.

The distal end of hollow tube 44 may be connected to opening 58 defined by first conduit 16 and the other end face 60 of the base 14. Second conduit 20 defines an opening 66 in end face 60.

As seen in FIG. 2, the underside of the annulus 40 has a plurality of circumferentially spaced openings 72. The openings 72 are connected to the interior passageways 50 and 54 in the annulus 40 and tube 44. If desired, instead of the openings 72 in the annulus, a circumferential groove 76 can be used as seen in FIG. 6.

As best seen in FIG. 3, the annulus 40 is circular in cross section. However, it is within the scope of the invention for the cross section to be circular or rectangular as seen in FIGS. 4 and 5. In the embodiment of the invention shown in FIG. 4, the openings 72 or groove 76 are on the flat side 80 of the "D". Similarly, in the embodiment of the invention illustrated in FIG. 5 by default openings 72 or groove are on the flat side 84 of the annulus.

As will be explained more fully herein the first conduit 16 helps to retain the template 36 on the anterior capsule during the capsulorhexis. The second conduit 20 is provided for introducing an irrigating liquid into the eye during the procedure to keep the anterior chamber formed if desired.

The surgical procedure in which the ophthalmic template 10 is used comprises connecting the first conduit 16 to a source of vacuum such as a syringe or a suitable bulb, or phaesemulsification machine. If desired, the second conduit 20 may be connected to a source of irrigating fluid. An incision of the eye is made to allow entry of the template 36 into the anterior chamber. Typically, the incision is no more than about three millimeters in length. The annulus 40 is squeezed to reduce its width. It is then inserted through the incision and placed over the anterior capsule in the location where it is desired to form the opening. A portion of tube 44 also extends through the incision. The vacuum will bring the surface of the annulus 40 into close contact with the anterior capsule. The vacuum may also flatten the annulus 40 to further define the inner edge 88 that is formed by the inner diameter of the annulus.

The surgeon can then remove the portion of the anterior capsule that is within the annulus 40. Since the surgeon is working within the annulus, the tearing tool will not slip. Further, there is a low likelihood that a poorly shaped or improperly located hole will be formed.

During the procedure irrigating fluid may be introduced into the anterior capsule to keep it formed through the second conduit 20 in base 14.

After the opening in the anterior capsule is made the tool can be withdrawn, the cataract removed and an artificial lens inserted in its place. Then the ophthalmic template 10 may be discarded.

What has been described is an ophthalmic template and a method for using it for cataract surgery. It offers the advantage of simplifying the procedure of cutting the anterior capsule so that surgeons having less skill can now perform it and to make it safer for patients. This is because they do not have to fear that they will make an oversized or undersized opening in the anterior capsule or that its edges will be of improper shape, or it will be in the wrong place.

While the invention has been described with respect to certain embodiments, it is apparent that other embodiments obviously skilled in the art in view of the foregoing description. Thus, the scope of the invention should not be limited by the description, but, rather, only by the scope of the claims appended hereto.

I claim:

1. An ophthalmic template for use in cutting an opening in the anterior capsule of the eye comprising a first member to be placed on the anterior capsule and having a shape that corresponds to the shape of the opening that is to be cut in the anterior capsule, and means for selectively retaining said first member on the anterior capsule, said last named means including means for connecting said first member to a source of vacuum.

2. An ophthalmic template for use in cutting an opening in the anterior capsule of the eye comprising an annulus to be placed on the anterior capsule, said annulus having an inner edge defined by the interior circumference of said annulus, said inner edge corresponding to the shape of the opening that is to be cut in the anterior capsule, and means for selectively retaining said annulus on the anterior capsule, said last named means including a hollow interior in said annulus and a plurality openings connected to said hollow interior.

3. A template as defined in claim 2 including means for connecting said interior of said annulus to a source of vacuum.

4. A template as defined in claim 2 wherein said annulus is comprised of a material that flattens under a vacuum.

5. An ophthalmic template for use in cutting an opening in the anterior capsule of the eye comprising an annulus to be placed on the anterior capsule, said annulus having an inner edge defined by the interior circumference of said annulus, said inner edge corresponding to the shape of the opening that is to be cut in the anterior capsule, and means for selectively retaining said annulus on the anterior capsule, said last named means including a hollow interior in said annulus and a circumferential groove connected to said hollow opening.

6. A template as defined in claim 5 including means for connecting said interior of said annulus to a source of vacuum.

7. A template as defined in claim 6 wherein said annulus is "D" shaped in cross section, and said circumferential groove is on the flat surface of said cross section.

8. A template as defined in claim 6 wherein said annulus is rectangularly shaped in cross section, and said circumferential groove is on the flat surface of said cross section that is adapted to be placed on the anterior capsule.

9. An ophthalmic template for use in cutting an opening in the anterior capsule of the eye comprising an annulus to be placed on the anterior capsule, said annulus being "D" shaped in cross section and the inner circumference of said annulus defining an inner edge that has a shape that corresponds to the shape of the opening that is to be cut in the anterior capsule, said annulus having a hollow interior and a plurality of openings connected to said interior, said openings being on the flat surface of said cross section for selectively retaining said first member on the anterior capsule.

10. An ophthalmic template for use in cutting an opening in the anterior capsule of the eye comprising an annulus to be placed on the anterior capsule, said annulus being rectangularly shaped in cross section and the inner circumference of said annulus defining an inner edge that has a shape that corresponds to the shape of the opening that is to be cut in the anterior capsule, said annulus having a hollow interior and a plurality of openings connected to said interior, said openings being on the flat surface of said cross section for selectively retaining said first member on the anterior capsule.

11. An ophthalmic template for use in cutting an opening in the anterior capsule of the eye comprising a first member to be placed on the anterior capsule and having a shape that corresponds to the shape of the opening that is to be cut in the anterior capsule, a base, said base supporting said first member and including a first conduit to be connected to source of vacuum for selectively retaining said first member on the anterior capsule, said first member having an outer surface with a plurality of openings and a hollow interior, said plurality of openings being connected to said hollow interior, and means for connecting said hollow interior of said first member to said first conduit.

12. A template as defined in claim 11 wherein said base includes a second conduit, and means for connecting said second conduit to a source of irrigation.

13. The method of making an opening in the anterior capsule of the eye comprising the steps of placing a template on the anterior capsule in the place where the opening is to be made, retaining said template in place by a vacuum, and removing the portion of said anterior capsule adjacent said template.

\* \* \* \* \*